US008403844B2

(12) United States Patent
Zhao-Wilson et al.

(10) Patent No.: US 8,403,844 B2
(45) Date of Patent: *Mar. 26, 2013

(54) METHODS FOR INTERVENTIONS

(75) Inventors: Xi Zhao-Wilson, Los Gatos, CA (US);
Paul C. Watkins, San Diego, CA (US);
Joseph M. Dhahbi, Alameda, CA (US)

(73) Assignee: BioMarker Pharmaceuticals, Inc., San Jose, CA (US)

( * ) Notice: Subject to any disclaimer, the term of this patent is extended or adjusted under 35 U.S.C. 154(b) by 1245 days.

This patent is subject to a terminal disclaimer.

(21) Appl. No.: 11/378,032

(22) Filed: Mar. 16, 2006

(65) Prior Publication Data

US 2007/0219418 A1    Sep. 20, 2007

(51) Int. Cl.
*A61B 5/00* (2006.01)
(52) U.S. Cl. .................................................. 600/300
(58) Field of Classification Search ........................ None
See application file for complete search history.

(56) References Cited

U.S. PATENT DOCUMENTS 6,406,853 B1 * 6/2002 Spindler ........................... 435/6

FOREIGN PATENT DOCUMENTS

WO    WO 03/88814 A2    10/2003

OTHER PUBLICATIONS

Friedman, The World Is Flat, 2005, Farrar, Straus and Giroux, New York, pp. 94-95.*
PCT Notification of Invitation to Pay Additional Fees, PCT/US2007/006564, mailed on Aug. 3, 2007 (9 pages).
Roth G S et al: "Caloric Restriction Mimetics: The next phase", Annals of the New York Academy of Sciences 2005 United States, vol. 1057, 2005 pp. 365-371.
Anisimov Vladimir N et al: "Effects of Phentermine and Phenformin on Biomarkers of Aging in Rats.", Gerontology 2005 Jan.-Feb., vol. 51, No. 1 Jan. 2005, pp. 19-28.
Dhahbi Joesph M et al: "Identification of potential caloric restriction mimetics by microarray profiling", Physiological Genomics, vol. 23, No. 3, Nov. 2005, pp. 343-350.
Valenzano et al: "Resveratrol Prolongs Lifespan and Retards the Onset of Age-Related Markers in a Short-Lived Vertebrate", Current Biology, Current Science, GB, vol. 16, No. 3, Feb. 7, 2006, pp. 296-300.
Bauer Johannes H et al: "An Accelerated assay for the identification of lifespan-extending interventions in *Drosophila melanogaster*", Proceedings of the National Academy of Sciences of the United States of America, vol. 101, No. 35, Aug. 31, 2004, pp. 12980-12985.
Sovak M: "Grape extract, resveratrol, and its Analogs: A Review", Journal of Medicinal Food 2001 United States, vol. 4, No. 2, 2001, pp. 93-105.
Seo D et al: "Genomic medicine: bringing biomarkers to clinical medicine", Current Opinion in Chemical Biology, Current Biology Ltd, London, GB, vol. 9, No. 4, Aug. 2005, pp. 381-386.
Ingram DK et al: "Calorie Restriction mimetics: an emerging research field", Aging Cell 2006 United Kingdom, vol. 5, No. 2, 2006, pp. 97-108.
PCT Notification of Transmittal of the International Search Report and the Written Opinion, PCT/US2007/006564, mailed on Oct. 17, 2007 (21 pages).
PCT Written Opinion for PCT Appln No. PCT/US2007/006564, mailed Sep. 25, 2008 (12 pages).

* cited by examiner

*Primary Examiner* — James Martinell
(74) *Attorney, Agent, or Firm* — Blakely Sokoloff Taylor & Zafman LLP

(57) ABSTRACT

Methods and systems for monitoring interventions and/or a subject, such as a human patient. One exemplary embodiment of a method includes measuring at least one biological parameter of a subject, determining a biological state from the measuring, administering (after the measuring) an intervention which includes a caloric restriction (CR) mimetic to the subject and measuring, after the administering, the at least one biological parameter and determining a later biological state from the measuring after the administering.

11 Claims, 2 Drawing Sheets

METHODS FOR INTERVENTIONS

BACKGROUND

Caloric restriction (CR) is a technique in which subjects, such as mice or humans, are fed a diet which has less than a "normal" amount of food for at least a certain period of time. Typically, the amount of food given in the diet is less than 40% of the minimum recommended daily amount measured in calories. The effects of a CR diet have been extensively studied, and numerous researchers have developed techniques to screen interventions, such as therapeutic substances or compounds, which when administered to a subject on a normal diet tend to cause the subject's physiological or biological state to mimic the state of an organism on a CR diet. Such interventions are referred to as CR mimetics because they cause the biological state of the organism receiving the intervention to mimic the state of a similar organism on a CR diet even if the organism is not on a CR diet. The effects of CR diets and techniques for screening for CR mimetics are described in the following patents and published applications which are hereby incorporated herein by reference: U.S. Pat. Nos. 6,406,853 and 6,569,624 and U.S. published applications 2005/0266438, 2005/0013776, 2004/0191775, 2004/0180003, 2003/0224360 and 2003/0124540.

Another area of biological research has involved the measuring of metabolites and/or biological states of a subject and monitoring those metabolites and states. The purpose of performing the measuring or monitoring is to predict or diagnose a disease or condition of the subject. This measuring may include measuring RNA, protein or metabolite abundances or activities in cells. Examples of such measuring or monitoring are described in the patent literature, including the following patents and published applications which are hereby incorporated herein by reference: U.S. Pat. No. 6,558,955 and U.S. published applications 2005/0181354 and 2004/0047896.

SUMMARY OF THE DESCRIPTION

Methods and kits for monitoring interventions or a subject are described. One exemplary method includes measuring at least one biological parameter of a subject, determining a biological state of the subject based upon the measuring, administering to the subject, after the measuring, an intervention which includes a caloric restriction mimetic, and measuring, after the administering, the biological parameter and determining a later biological state from the measuring. In at least certain embodiments, the at least one biological parameter is a gene expression parameter (e.g. a measured amount of an mRNA transcript) or a metabolite measurement or a peptide measurement (e.g. a concentration of a protein in the cytoplasm of certain cells). This exemplary method may further include predicting whether the subject is a good candidate for an intervention with a CR mimetic. The determining of the biological state may involve determining whether the subject's state resembles that of a similar subject on a CR diet; for example, this determining may include comparing gene expression measurements obtained from the measuring of the subject to known gene expression measurements for genes known to be effected by CR. The exemplary method may further include modifying the intervention after determining that the later biological state matches a predetermined state (e.g. a CR state or a non-CR state). In at least certain embodiments of this exemplary method, the administering of the CR mimetic is in response to determining that the subject is not in a CR state of gene expression such that the administering will not occur if the subject is in a CR state. The CR mimetic may be determined before the method by the use of screening techniques known in the art.

Another exemplary method includes determining whether a subject is in a CR state and determining, if the subject is not in a CR state, if the subject is a good candidate for an intervention which includes a CR mimetic.

Also described are for instituting CR diets for short periods of time and monitoring CR markers to determine when to interrupt the CR diet (and resume a normal caloric intake diet) and when to interrupt the normal diet (to then resume a CR diet). Methods of monitoring longer term CR diets are also described.

Kits which include assay materials and/or equipment to perform one or more of the methods described herein are also within the scope of the interventions.

BRIEF DESCRIPTION OF THE DRAWINGS

The present invention is illustrated by way of example and not limitation in the figures of the accompanying drawings in which like references indicate similar elements.

DETAILED DESCRIPTION

Figure 1:
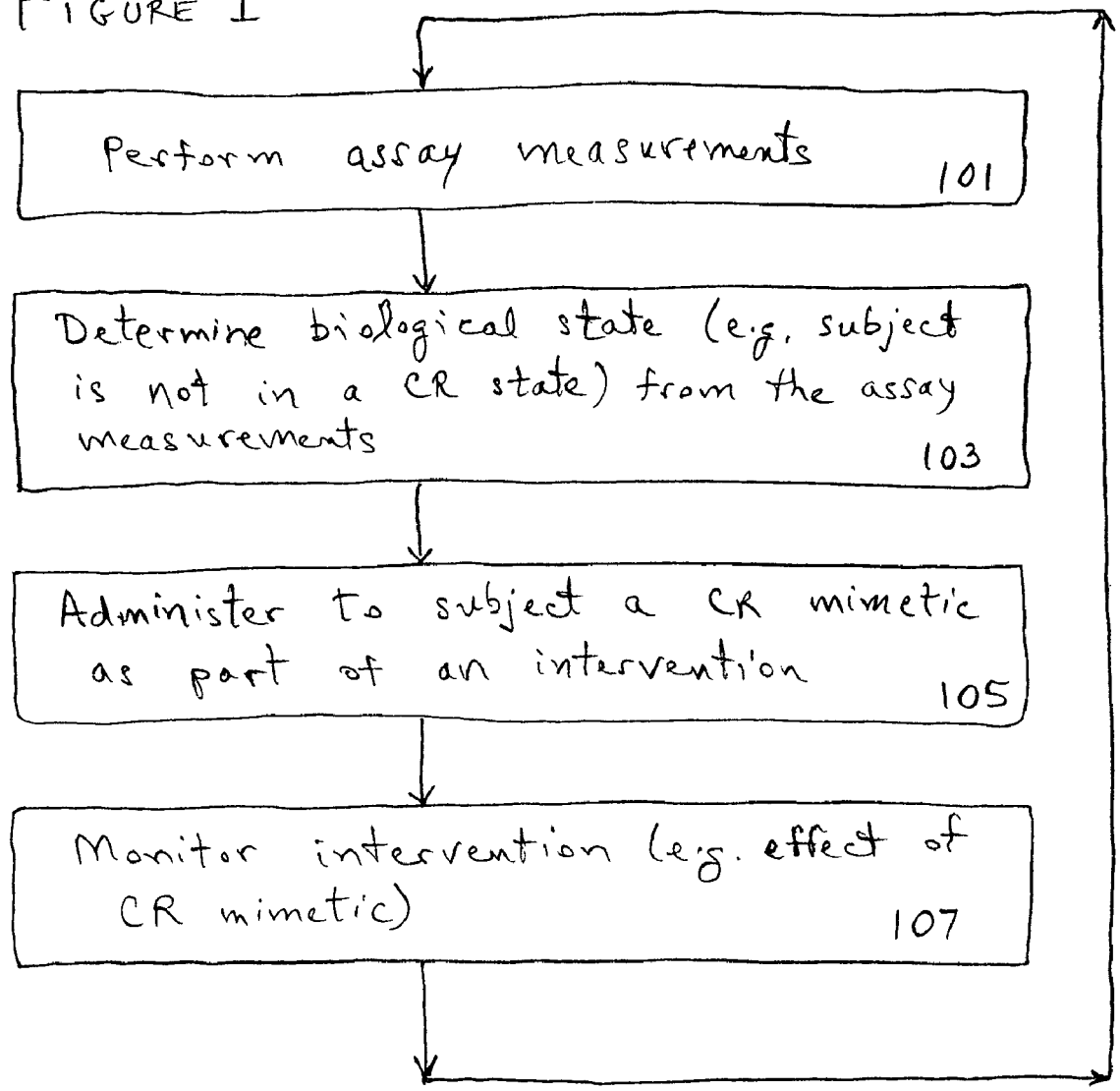
FIG. 1 is a flow chart which shows one exemplary method of the present inventions.

The subject invention will be described with reference to numerous details set forth below, and the accompanying drawings will illustrate the invention. The following description and drawings are illustrative of the invention and are not to be construed as limiting the invention. Numerous specific details are described to provide a thorough understanding of the present invention. However, in certain instances, well known or conventional details are not described in order to not unnecessarily obscure the present invention in detail.

The various methods described herein may make use of known assaying techniques such as those described in U.S. Pat. No. 6,558,955 and U.S. published applications 2005/0181354 and 2004/0047896, and this patent and both of those applications are incorporated herein by reference. The assay techniques may include measuring mRNA transcript concentrations of mRNA transcripts known to be effected by a CR diet or may include measuring concentrations of the gene products (e.g. polypeptides) of those transcripts or may include measuring the concentrations of metabolites involved in metabolic pathways which are effected by those gene products. Other types of assay techniques, such as other assay measurements, may also be used. The assay measurements may also include measurements of gene expression (e.g. mRNA transcript concentrations) for genes not effected by a CR diet (which is often characterized as a diet which supplies less than 35% of the recommended daily caloric intake) or unrelated to CR, and may also include measurements of gene products of such genes and/or metabolites involved in metabolic pathways which are effected by such gene products. Moreover, the assay measurements may include conventional physiological measurements such as blood glucose concentration, $O_2$ partial pressure (in blood) levels, red blood cell count, etc. One or more of the foregoing measurements may be used in the methods of FIGS. 1 or 2 in operations 101 and 201 respectively. The methods of FIGS. 1 and 2 will now be described further.

Operation 101 involves the assay measurements described above. Typically, in at least certain embodiments, these measurements will include measurements of mRNA transcript concentrations for genes known to be effected by a CR diet and/or a known CR mimetic, and these measurements will then permit a determination of whether the subject (e.g. a human patient which provided the samples used to make the measurements) is in a biological state which resembles a state of a similar subject on a CR diet (in other words, whether the measured subject is in a CR state). The samples taken from the subject being measured may be blood samples or cell samples which are then used to perform one or more of the measurements described.

After the measurements are done, a determination, in operation 103, of the biological state of the subject is made using the information from the measurements. This information may indicate, for example, that the subject is not in a CR state (as shown by a comparison of measurements of the concentration of various mRNA transcripts, of the subject, with measurements of concentrations of mRNA transcripts of a plurality of genes known to be effected by a CR diet and/or a CR mimetic). Alternatively, the information may indicate other biological states (e.g., the patient has diabetes or is in a CR state or has Alzheimer's disease). It will be appreciated that, in certain embodiments, the measurements may be just conventional physiological assays which do not include measurements for CR related genes. In one embodiment of a method shown in FIG. 1, the determination of whether the subject is not in a CR state is used to decide whether to administer a CR mimetic in operation 105; in other words, if it is determined, in operation 103, that the subject is not in a CR state then the CR mimetic is administered in operation 105, but if the subject is in a CR state then the CR mimetic is not administered and the method skips back to operation 101 (and these operations 101, 103 and back to 101 may be repeated over time).

The administration, in operation 105, of the CR mimetic may use known dosages and formulations to administer one or more CR mimetics. It will be appreciated that known techniques for screening for CR mimetics and testing their efficacy and safety may be employed and are described in, for example, the following patents and published applications, all of which are incorporated herein by reference: U.S. Pat. Nos. 6,406,853 and 6,569,624 and U.S. published applications 2005/0266438, 2005/0013776, 2004/0191775, 2004/0180003, 2003/0224360 and 2003/0124540. The CR mimetic may be administered only once or repeatedly over time (e.g. one dosage per day, etc.). As the CR mimetic is administered, operation 107 may be used to monitor the effect of the CR mimetic. This monitoring may involve conventional physiological measurements and it may precede returning to operation 101 as shown in FIG. 1 or it may be part of repeating operation 101. The method of FIG. 1 may be used to monitor a patient's wellness state and to treat the state to improve the patient's state using CR mimetic.

Figure 2:
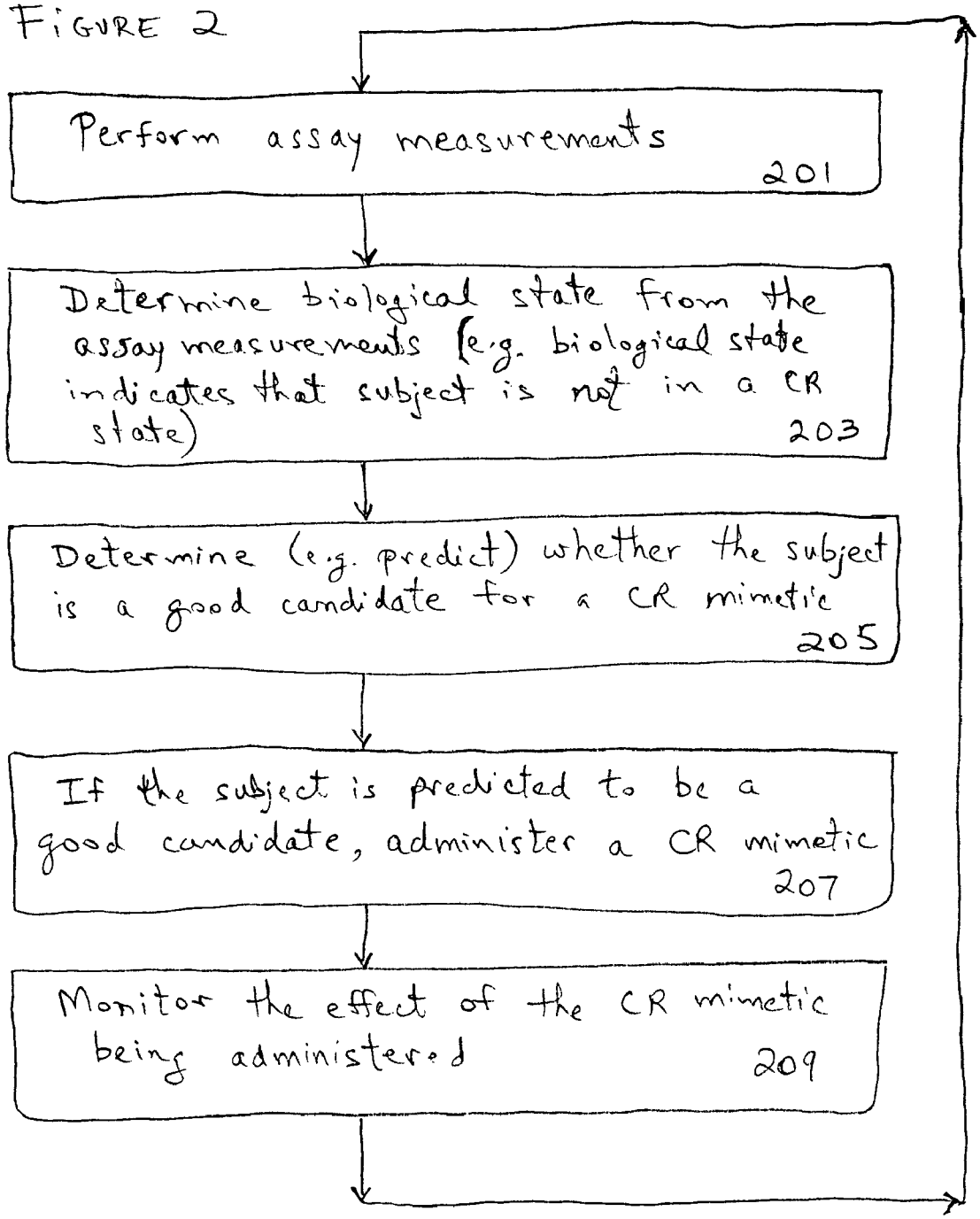
FIG. 2 is a flow chart which shows another exemplary method of the present inventions.

FIG. 2 shows another exemplary method of the inventions. It can be seen by comparing FIGS. 1 and 2 that operations 201, 203 and 209 are similar to operations 101, 103 and 107 respectively and hence no further discussion of operations 201, 203 and 209 is needed. Operation 205 involves the determination, usually through a prediction, of whether the subject is a good candidate (e.g. the subject is more likely than not to respond favorably to a treatment with one or more CR mimetics). This prediction may involve comparing the subject's measurements from operations 201 and 203 to measurements of other subjects who responded favorably to prior treatments with one or more CR mimetics. If the prediction suggests a positive response to a CR mimetic then operation 207 would normally follow.

In operation 207, a CR mimetic is administered if the subject is predicted to be a good candidate for a CR mimetic. Operation 209 normally follows operation 207, and operation 209 involves monitoring the effect of the CR mimetic which is being administered, and this operation 209 normally returns to operation 201. Operation 209 may alternatively be part of operation 201.

Another aspect of the inventions relates to monitoring, through testing (such as gene expression assays to determine gene expression levels of genes known to be effected by CR), of individuals that have already subjected themselves to caloric restriction. This monitoring may be used as a way to determine whether or not such individuals are achieving a desirable result (e.g., a C.R. state) based on the results of the testing. For example, a person who is already on a CR diet (either for a short period of time, such as 2-4 months, or for many years, such as 2 to 5 years or longer) may use a kit to perform the testing to determine whether the person is achieving a desired result, such as a CR state, as indicated by the results of the testing. This testing may be conventional physiological tests in combination with gene expression level assays (of genes known to be effected by a CR diet or a CR mimetic, which may be referred to as "CR markers") or it may include merely the gene expression level assays. Alternatively, rather than using gene expression level assays, the testing may use other assay measurements such as measurements of gene products (e.g. proteins) and/or metabolites involved in metabolic pathways which are effected by such gene products. A monitoring test, in the forum of a kit containing the assay reagents and test substrates and measuring devices, would be useful to such a person to him such person determine whether or not they are meeting their goals (e.g. their various gene expression levels or other biochemical changes are highly correlated with a CR state as indicated by measurements made with the kit).

The intermittent use, with monitoring, of a CR diet is another aspect of the inventions. For example, a person may institute a CR diet and maintain the CR diet for a short period of time (e.g. 5 weeks or 2 months) and then interrupt the CR diet (by resuming a normal caloric intake diet for a short period of time) and then institute, again, the same (or different) CR diet and again maintain this next CR diet for another short period of time and then interrupt, again, the CR diet for a short period of time and then repeat this process again. In doing so, the person may monitor the effect of the CR diet by using a kit to measure CR markers, such as gene expression levels of genes known to be effected by a CR diet or known CR mimetics or gene products of such genes or metabolites involved in biochemical pathways which use those gene products. Such monitoring may allow the person to help to determine the length and stage of such an intermittent CR diets; such monitoring could be repeated over intervals of time during at least some of the time that the CR diets are maintained and also during at least some of the time that the CR diets are maintained and also during at least some of the time that the CR diets are interrupted. For example, while on an intermittent, short term CR diet, the monitoring may be performed (e.g. using a kit which includes reagents and/or equipment to measure CR markers) while on the CR diet, and the testing could be repeated over the time of the short term CR diet until a desired set point (which is indicated by the monitoring) has been reached, and after this get point (e.g. a new CR state) is reached, then resuming a normal diet (e.g. normal caloric consumption) for a short period of time during which monitoring is performed to determine when the CR markers move out of an optimal or desired range, and when these CR markers do move out of that range, then resuming another short term CR diet while again, monitoring CR markers during the short term diet. This CR diet to normal diet to CR diet cycle may be repeated with monitoring being used to indicate when to institute and when to interrupt a CR diet.

What is claimed is:

1. A method for monitoring interventions, the method comprising:
    measuring at least one biological parameter of a subject;
    determining a biological state from the measuring;
    administering, after the measuring, an intervention which includes a Caloric Restriction (CR) mimetic to the subject;
    measuring, after the administering, the at least one biological parameter and determining a later biological state from the measuring after the administering; and
    modifying the administering of the intervention, after determining the later biological state, based on the later biological state.

2. A method as in claim 1 wherein the at least one biological parameter is a gene expression parameter representative of a level of expression of a gene.

3. A method as in claim 1 wherein the at least one biological parameter is one of a metabolite measurement or a peptide measurement.

4. A method as in claim 1 further comprising:
    predicting whether the subject is a good candidate for an intervention with a CR mimetic.

5. A method as in claim 1 further comprising:
    determining, through a plurality of gene expression measurements of the subject, whether the subject's gene expression state mimics a CR state of gene expression.

6. A method as in claim 1 wherein the determining the biological state comprises comparing gene expression measurements obtained from the measuring of the subject to known gene expression measurements for genes known to be affected by CR.

7. A method as in claim 1 wherein the administering, after the measuring, is in response to determining that the subject is not in a CR state of gene expression, and wherein the CR mimetic has been determined to be a mimetic of CR through a screening procedure.

8. A method as in claim 1 wherein if the later biological state does not mimic a CR state then discontinuing the administering of the intervention.

9. A method for monitoring a subject, the method comprising:
    determining whether the subject is in a Caloric Restriction (CR) state;
    determining, if the subject is not in a caloric restriction state, if the subject is susceptible to an intervention which includes a CR mimetic by comparing gene expression data from the subject to gene expression data of subjects known to respond positively to a CR mimetic prior to administering the intervention which includes the CR mimetic.

10. A method as in claim 9 wherein the determining whether the subject is in a CR state comprises comparing gene expression measurements obtained from the subject to known gene expression measurements for genes known to be affected by CR.

11. The method of claim 9 further comprising:
    administering the intervention which includes the CR mimetic to a subject determined to be susceptible to the intervention.

* * * * *